United States Patent [19]

Fenzlein et al.

[11] Patent Number: 5,425,361
[45] Date of Patent: Jun. 20, 1995

[54] APPARATUS FOR THE DETERMINATION OF MEDICAL, ELECTRO-CHEMICAL MEASURED VALUES RELEVANT TO ORGANIC OR METABOLIC FUNCTIONS

[75] Inventors: Paul-Gerhard Fenzlein, Elsa-Brandströmstrasse 33, D-8500 Nürnberg 80; Wolfgang Anderer, Aurachtal, both of Germany

[73] Assignee: Paul-Gerhard Fenzlein, Germany

[21] Appl. No.: 983,665

[22] Filed: Nov. 30, 1992

[30] Foreign Application Priority Data

Nov. 28, 1991 [DE] Germany ............... 41 39 122.5

[51] Int. Cl.⁶ ............................................. A61B 5/05
[52] U.S. Cl. ............................ 128/635; 128/639; 128/736
[58] Field of Search ............... 128/903, 632, 635, 637, 128/734, 736, 763, 770, 771; 235/375; 604/38, 51, 52, 404; 204/407

[56] References Cited

U.S. PATENT DOCUMENTS

| | | | |
|---|---|---|---|
| 3,646,606 | 2/1972 | Buxton et al. | 128/670 |
| 4,301,807 | 11/1981 | Mentelos | 128/635 |
| 4,431,004 | 2/1984 | Bessman et al. | 128/635 |
| 4,519,401 | 5/1985 | Ko et al. | |
| 4,543,955 | 10/1985 | Schroeppel | |
| 4,642,636 | 2/1987 | Smith et al. | |
| 4,685,465 | 8/1987 | Klitgaard et al. | 128/635 |
| 4,690,147 | 9/1987 | Ooe, et al. | |
| 4,706,689 | 11/1987 | Man | |
| 4,729,824 | 3/1988 | Giner | 128/635 X |
| 4,786,394 | 11/1988 | Enzer et al. | 204/407 X |
| 4,935,875 | 6/1990 | Shah et al. | 235/375 X |
| 5,000,180 | 3/1991 | Kuypers et al. | 128/635 |
| 5,007,424 | 4/1991 | Ahsbahs et al. | 128/635 |
| 5,080,106 | 1/1992 | Sekii et al. | 128/692 |
| 5,126,937 | 6/1992 | Yamaguchi et al. | 128/635 X |

FOREIGN PATENT DOCUMENTS

| | | |
|---|---|---|
| 0403904 | 12/1990 | European Pat. Off. . |
| 0074498 | 8/1992 | European Pat. Off. . |
| 2630958 | 7/1978 | Germany . |
| 3142468 | 6/1982 | Germany . |
| 3116690 | 9/1983 | Germany . |
| 3535642 | 7/1986 | Germany . |
| 3446248 | 8/1986 | Germany . |
| 3505342 | 8/1988 | Germany . |
| 3544095 | 5/1989 | Germany . |
| 3725597 | 5/1989 | Germany . |
| 3941169 | 7/1990 | Germany . |
| 3917876 | 12/1990 | Germany . |
| 3921962 | 1/1991 | Germany . |
| 3926630 | 7/1991 | Germany . |
| 2183342 | 6/1987 | United Kingdom . |
| WO921775 | 10/1992 | WIPO . |

OTHER PUBLICATIONS

"Maschinenlesbar: Schlussel, Ausweis Geldersata" *Funkschau* vol. 13, 1986, pp. 24–28.
"Sensor und Signalverarbeitung auf einen Chip-Entwicklungstendenzen und Risiken" *Technisches Messen tm* vol. 2, 1986 (Opermeier).
"Kalibriertechnik fur Gassensoren " *Technisches Messe tm* vol. Nov. 1990 (Pichlmaier).

*Primary Examiner*—Lee S. Cohen
*Assistant Examiner*—Samuel Gilbert
*Attorney, Agent, or Firm*—Laff, Whitesel, Conte & Saret, Ltd.

[57] ABSTRACT

A measuring apparatus for the determination of medical, electro-chemical measured values relevant to organic or metabolic functions comprises a sensor head, a coupling, to which the sensor head is exchangeably secured, and a microprocessor-controlled base instrument, which is provided with a central control unit, with a data detection and evaluation unit to detect and convert the measuring signals forwarded by the coupling in accordance with an in each case associated calibrating regulation, with a display to display the measured values and with a keyboard to enter measuring-relevant data. The sensor head with its measuring electrodes is precalibrated to standard when manufactured, the calibrating regulations in each case associated with a certain measuring electrode being stored in the base instrument and the data detection and evaluation unit, controlled by a corresponding external entry at the base instrument, having access to the calibrating regulations associated with the measuring electrodes in each case located in the sensor head when a sensor head is used for measuring.

6 Claims, 3 Drawing Sheets

APPARATUS FOR THE DETERMINATION OF MEDICAL, ELECTRO-CHEMICAL MEASURED VALUES RELEVANT TO ORGANIC OR METABOLIC FUNCTIONS

FIELD OF THE INVENTION

The invention relates to an apparatus for the determination of medical, electro-chemical measured values relevant to organic or metabolic functions with a sensor head with miniaturized measuring electrodes adapted to the measured values to be determined, a temperature sensor and one or several reference electrodes, a coupling, to which the sensor head is exchangeable secured and which has corresponding lines to lead off the electric measuring signals furnished by the measuring electrodes and the sensors, a microprocessor-controlled base instrument, which is provided with a central control unit with a working, program and data memory to control the operational processes within the apparatus, a data detection and evaluation unit to detect and convert the measuring signals forwarded by the coupling in accordance with an in each case associated calibrating regulation, a display to display the measured values determined by the data detection and evaluation unit, and a keyboard to enter measuring-relevant data.

BACKGROUND OF THE INVENTION

Fundamentally, objective measuring parameters for the determination of the organic and metabolic functions exist in medicine and in particular in emergency and intensive care and surgery. These parameters are for instance electro-chemical values. By way of example attention is drawn to the very important metabolism taking place under the participation of oxygen in tissues and organs for the supply of body cells with oxygen. Within the scope of the oxygen supply of the organism and the effects depending thereon, a lack of oxygen may for instance occur in a tissue, which will lead to a modification of the electrolytic activities on the cell membrane (ischemia). Such a lack of oxygen is accompanied by an increase of the potassium activity outside the cell, while simultaneously the sodium activity decreases and the tissue pH value drops. Thus, potassium and sodium activities as well as the tissue pH value are possible electrochemical measured values for the determination of the supply of a tissue with oxygen. Any modifications beyond this can equally be detected by way of electromyelography (EMG) with the aid of enzyme electrodes for the detection of glucose, lactate or similar metabolic products by ampereometric sensors.

Pathologically conditioned edema in the tissue are a further example giving rise to disturbances of the microcirculation, i.e. of the capillary blood circulation, to a pathological modification in the capillary wall and the inter-cell chamber (interstitium) and thus to similar metabolic modifications as described above. Here, too, the above-mentioned measuring methods can furnish good clues for diagnosis and therapy.

For the determination of the above electro-chemical measured values mentioned by way of example, suitable measuring methods and apparatuses working on a potentiometric or ampereometric base have fundamentally been known for a long time. However, these measuring methods and apparatuses have essentially been applied only within the scope of laboratory tests, for which samples of the tissue of interest have to be available.

By comparison, with a view to emergency and intensive care and surgery it is desirable for such measuring methods to be applied "in vivo"—for instance directly during an operation—with the aid of suitable measuring apparatuses, so that the surgeon gets important prompt information on the efficiency of his steps and on the condition of the organ operated within the scope of "on-line" diagnostics.

An apparatus of the generic type developed to this end is already known from German patent 37 25 597. With this apparatus for measuring the ion activity, a sensor head with miniaturized measuring electrodes adapted to the type of ions to be determined can be applied to the surface of a tissue, for instance an organ surface, and the activity of the ions of interest can be measured with the aid of ion-selective membranes in the vicinity of the measuring electrodes.

Upon contact of the ion-selective membrane with the medium containing the corresponding ions, an electromotive force or an electro-chemical potential EMF can be measured by way of lines from the membrane, which is also given by the NERNST equation qualitatively reproduced as follows, $$EMF = E_0 - C\ T\ lg\ a_{ion}$$

with $E_0$: reference potentional, C: scale factor, T: temperature and $a_{ion}$: ion activity.

On the basis of this relation the ion activity can be detected based on a potentiometric measurement.

Applied in practise, the measuring apparatus basically known from the above-mentioned publication involves problems in particular with regard to calibration and any subsequent measurements. As it is, prior to being used for measuring, each measuring electrode of the sensor must be calibrated in a time-consuming way, i.e. a calibration curve must be prepared of the electromotive force as a function of the ion activity at a certain temperature or a number of certain temperatures. Proceeding from this calibration curve an electromotive force measured at a corresponding temperature can be converted into a corresponding ion activity. The necessary calibration is a complicated preparatory step for measuring, it is time-consuming and thus conflicting with real "on-line" diagnostics. Furthermore, the known sensor has implied regular subsequent calibrations to take place in between the measurements for correction of the measured values. Moreover, measurement in different temperature ranges is not possible with the known measuring apparatus without prior calibration at a corresponding measuring temperature, which complicates its use in organ transplantation surgery, where stored donated organs are kept strictly cooled.

SUMMARY OF THE INVENTION

Proceeding from the described problems with measuring apparatuses of the prior art, it is an object of the invention to further develop a measuring apparatus of the generic kind such that simple, automated and prompt measurement of the most different measured values is possible without any substantial expense of calibration.

This object is attained by an apparatus wherein the sensor head with its measuring electrodes is precalibrated to standard by the manufacturer and wherein the calibrating regulations associated with a certain measuring electrode are stored in the base instrument, the data detection and evaluation unit, controlled by a corresponding external entry at the base instrument, having access to the calibrating regulations associated with the measuring electrodes in each case located in the sensor head when a sensor head is used for measuring. By consequence, the sensor head with its measuring electrodes is pre-calibrated to standard by the manufacturer, i.e. the measuring electrodes have defined electro-chemical properties. Due to this standardization, calibrating regulations associated with the respective measuring electrodes can be stored in the base instrument in a corresponding memory making the expensive calibration of a sensor head for measuring purposes unnecessary. For the correct conversion of the measured potential values into, for instance, an ion activity, while a sensor head is used for measuring, it is sufficient to communicate, controlled by a corresponding external entry at the base instrument, to the data detection and evaluation unit of the base instrument what kind of measuring electrodes are integrated in the sensor and which of the calibrating regulations stored to access for the conversion.

Due to the steps specified above, the use of a measuring apparatus according to the invention and of the associated sensors and measuring electrodes becomes possible in many fields of medicine, such a measuring apparatus being particularly simple to operate and assuring prompt measurements. Diagnoses, therapies and operations are not prolonged or handicaped by the use of the measuring apparatus.

Due to the preferred embodiments of the invention, the control of the access that the data detection and evaluation unit may have to the calibrating regulation corresponding to the respective sensor head can take place either by a code representative for each sensor being entered via the keyboard of the base instrument or by a bar code applied to the sensor or the latter's wrapping being scanned by a bar code reader connected with the base instrument. Magnetic stripes or memory chips integrated in the sensor head and to be fetched externally are also possible for the encoding or storing of corresponding data.

Especially high measuring accuracy, in particular within a wide range of temperature from for instance slightly above the freezing point to body temperature, is achieved by another preferred embodiment of the invention, wherein, when manufactured, the sensor head with its electro-chemical measuring electrodes is pre-calibrated to standard such that in the activity-potential reference diagram the isothermal point of each measuring electrode lies in each case within the activity corridor associated with the measuring electrode. Thereby, use is made of the recognition that the electrochemical properties of each measuring electrode are defined, through its $E_0$ potential and the scale factor C, as parameters into which enters the manufacturer's adaptation of the miniaturized measuring electrodes. These two parameters determine the so-called isothermal point. If the latter is within the range of activity to be measured by the electrode, measurements in the most different temperature ranges will allow for a conversion of the potential value into a corresponding value of ion activity to take place at a particularly low scaling error. Thus, no special calibration is necessary for the temperature correction with measurements of ion activities or also of metabolic products (for instance bicarbonate, $pCO_2$, $pO_2$ and the like), since due to the afore-mentioned standardization of the measuring electrodes, all the necessary data on the reference potential $E_0$ in the NERNST equation and on the corresponding isothermal point of each respective measuring electrode are known to the measuring system via the encoding of the sensor.

The subsequent calibration of the apparatus according to another preferred embodiment of the invention is a controlling measure for reasons of safety.

During the subsequent calibration by means of calibrated reference solutions at a defined temperature, the measuring apparatus will advantageously automatically realize by variance comparison whether the measuring electrodes of the sensor head respectively used really behave in conformity with the standardized pre-calibration. If, during variance comparison and by reason of instabilities of the measuring electrodes, only slight deviations in the sense of an additive offset result in the dependence of the measured potential value on the respective activity, this deviation—if not within a certain tolerance—can be compensated by computation by the data detection and evaluation unit. If the actual values found during the subsequent calibration are intolerably distant from the set values, the measuring apparatus can automatically stop the measuring process or it can at least signal that the sensor head presently in use does not function.

Advantageously, further physical sensors may be integrated in the sensor head such as pressure absorbers, flowmeters, optical measuring devices and electromyelography electrodes. This makes the apparatus according to the invention a multifunctional measuring system equal to the most different measuring objects, the calibrating expense in this case, too, being reduced to zero by pre-calibration by the manufacturer or being reduced at least to such extent that it does not handicap the rapid use of the sensors. In this context flow measurements with the aid of miniaturized ultrasonic sensors are to be mentioned by way of example. If a sensor head according to the invention has miniaturized membrane electrodes for potentiometric measurement of the electrolytic activity as well as a miniaturized flowmeter in the form of an ultrasonic sensor, then the microcirculation of blood or of extra- or intracellular perfusion solutions in certain tissue areas of the organ can be controlled by the flow measurement as well as the measurement of electrolytic activity independently one from the other for instance in transplantation organs, when the organ is taken out of the donor's body, when it is stored and implanted into the receiver's body. Thus, referring to different parameters a safe control of such an organ is ensured. In this context it must be added that also a corresponding flowmeter can be subsequently calibrated without any special expense, since during the above-mentioned subsequent calibration by means of calibrated reference solutions the flow within the latter is zero and the flow value found during the reference measurement can be made equal to zero without any difficulty.

According to a preferred embodiment of the invention the coupling may for instance be connected with the base instrument via a multicore electric cable connection. The coupling is then preferably in the form of a handle.

According to another preferred embodiment of the invention the coupling with a sensor head is formed as an implantable sensing element, with the aid of which a continuous control of the most important organic and metabolic functions of somebody seriously ill in the intensive care department becomes possible without any substantial stress for the patient and without any restriction for the medical staff. The sensing element is a complex unit, into which a suitable voltage supply and measuring electronics with a measuring amplifier for impedance transformation, an analog-to-digital converter and measured-value conversion means are integrated as well as suitable telemetry means. The values measured by the sensor head are converted to be telemetrically transferable in the coupling and are then transferred via the telemetric transmitter in the coupling to the telemetric receiver in the base instrument.

By embodying the apparatus according to another aspect of the invention, wherein the sensor head is in the form of a flow cell, it is possible to take measurements in the blood by means of the apparatus, there being no necessity of disposing of the blood after measuring.

Further features, details and advantages of the invention will become apparent from the ensuing description of an example of embodiment taken in conjunction with the drawing.

DESCRIPTION OF THE PREFERRED EMBODIMENT

Figure 1:
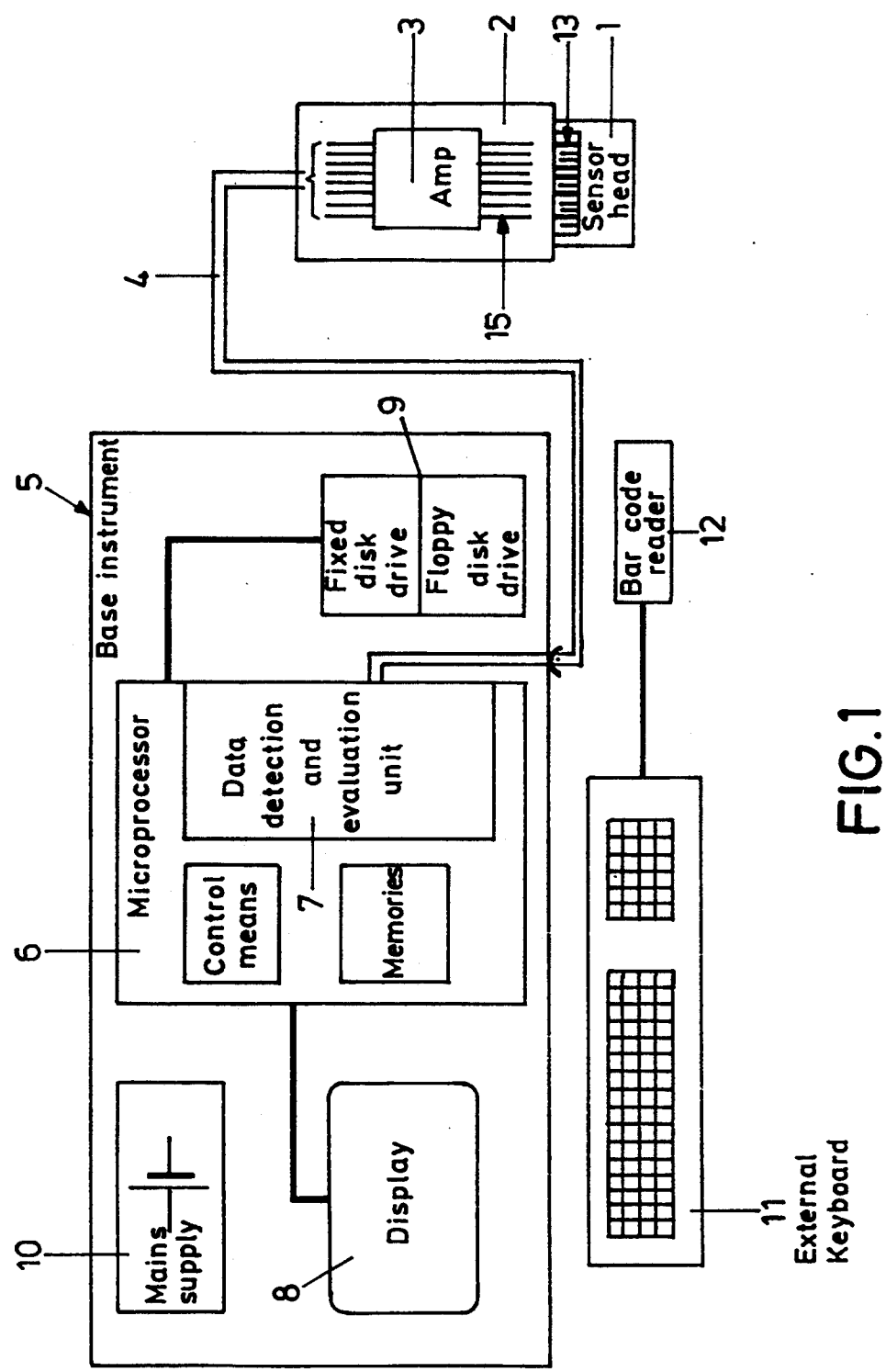
FIG. 1 is a block diagram of a measuring apparatus according to the invention.

A measuring apparatus according to the invention for the determination of medical, electro-chemical measured values relevant to organic or metabolic functions has a sensor head 1 exchangeably secured by plug connection to a coupling 2 in the form of a handle. A measuring amplifier 3 is integrated in the sensor head for amplification and impedance transformation of the as a rule high ohmic measuring signals from the sensor head 1. By way of a multicore cable 4 the coupling 2 is in connection with the measuring input of a base instrument 5 having, as a central control unit, a microprocessor 6 with corresponding working, data and program memories. Further, a data detection and evaluation unit 7 is provided in the base instrument 5 to detect and convert the measuring signals forwarded by the coupling 2. Further, a display 8 in the form of a liquid crystal screen is provided as well as a fixed disk and floppy disk drive 9 and a usual mains supply 10.

Measuring or patient relevant data can be entered via an external keyboard 11. A bar code reader 12, by means of which the data put down in the bar code 13 on the sensor head 1 can be entered into the base instrument 5 via the measuring electrodes of the sensor head, is further connected with the base instrument 5 by means of this keyboard 11.

Figure 2:
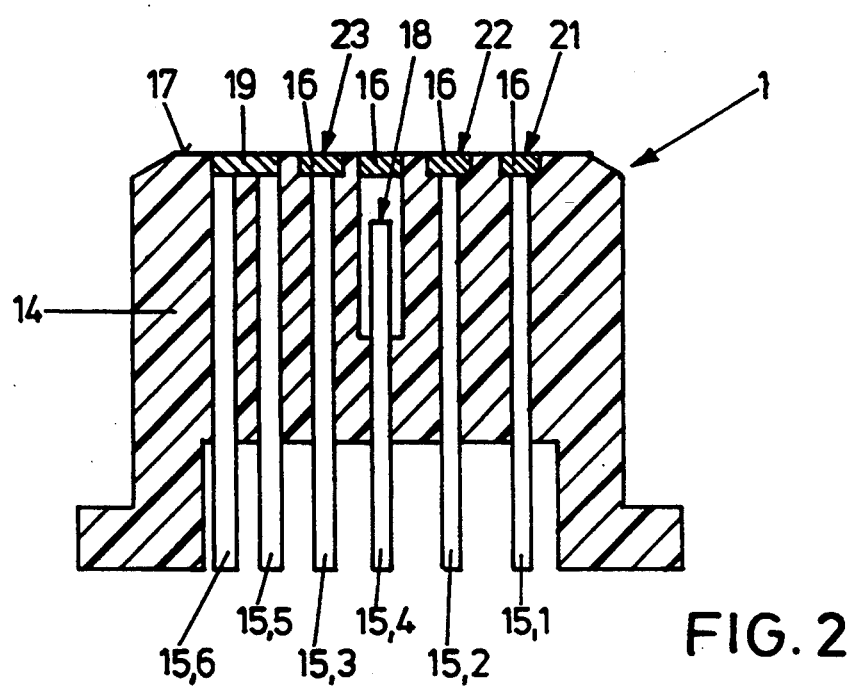
FIG. 2 is a diagrammatic longitudinal section through a sensor head of the apparatus according to FIG. 1.
Figure 3:
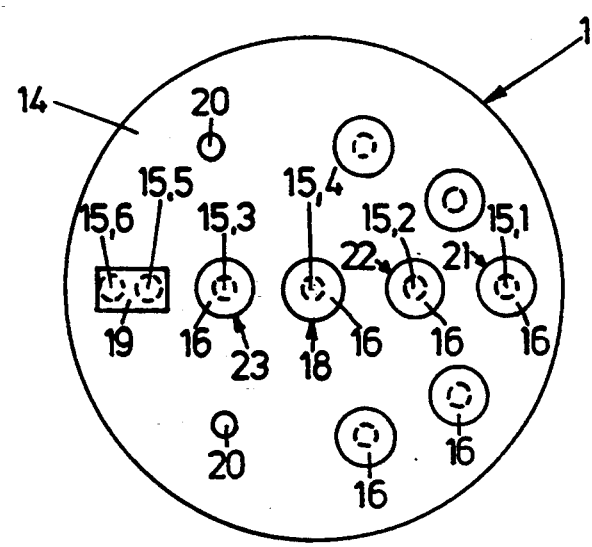
FIG. 3 is a view of the front of the sensor head according to FIG. 2.

The sensor head shown in FIGS. 2 and 3 consists of an essentially cylindrical body 14 of PVC or polyurethane full plastic material, into which different electric lines 15 are embedded in the form of silver wires. Other precious metals, such as gold or platinum, can also be used for the lines 15. Together with ion selective membranes 16 inserted in recesses in the front 17 of the body 14 the lines 15.1, 15.2 and 15.3 form ion selective measuring electrodes for potentiometric and ampereometric measurements. The membranes 16 are PVC matrix membranes. A reference electrode 18 is arranged centrally into the body 14 and its reference potential is feedable via the line 15.4 to the coupling 2 and thus to the data detection and evaluation unit 7 in the base instrument 5. A Pt 100 resistor is connected as a temperature sensor via the lines 15.5 and 15.6. As seen in FIG. 3, further sensors 20 for instance for electromyelography (EMG) or enzyme electrodes for the determination of glucose or lactate concentration are embedded into the body 14 and end in the front 17.

The measuring electrodes 21, 22, 23 formed by the membranes 16 in connection with the associated lines 15.1 to 15.3 serve for instance to measure the activity of potassium or sodium ions and to measure the pH value.

In the following the functioning of the apparatus according to the invention is explained on the basis of the potassium sensitive measuring electrode 21. When manufactured the measuring electrode 21 is made such that it exhibits the dependence shown in FIG. 4, of the measuring potential EMF furnished by it on the ion activity $a_K$ and on the temperature. The manufacturing layout of measuring electrodes in general and of the measuring electrode 21 in particular with a typical $E_0$ potential, a scale factor C and an isothermal point 24 is ensured in that on the one hand, the lines 15 in their surface quality and dimensioning and on the other hand, the membranes 16 in their dimensioning and high ohmic impedance lie within narrow tolerances in terms of reproducibility. On the part of the manufacturer sensor heads 1 with standardized measuring electrodes are produced which exhibit a dependence shown in FIG. 4, of the furnished measuring potential EMF on the ion activity $a_K$ and on the temperature with a characteristic $E_0$ potential, a scale factor C and an isothermal point 24. The latter is defined by the point of intersection of the different temperature-dependent measured lines of the diagram shown in FIG. 4 and lies about in the middle of the activity measuring range associated with a measuring electrode and which is approximately outlined by the corridor M according to FIG. 4. The values detected during pre-calibration for the $E_0$ potential and the scale factor C—both parameters determine the isothermal point of intersection 24—are put down in an encoded form in the bar code 13 and are thus available as input information for the base instrument 5.

For instance, the NERNST equation given at the outset can then be stored qualitatively as a calibrating regulation stored in the data detection and evaluation unit 7, the quantification defining the precise potential-activity dependence being effected by reading the bar code 13 prior to the sensor head 1 being used for measuring. Since the sensor head can simultaneously measure the temperature prevailing while the measurement is taken, the data detection and evaluation unit 7 can compute a measuring potential EMF with the aid of the stored calibrating regulation for instance in the form of the NERNST equation, and the corresponding ion activity with the aid of the read-in information on the $E_0$ potential and on the scale factor C, which can be visualized on the display 8 or stored on the fixed disk and floppy disk drive 9 for further processing or documentation.

Summing up, it may be said that with the help of the pre-calibration of the measuring electrodes 21 to 23, measuring of the ion activity can take place within a temperature range of about 0° C. to 40° C.

Figure 4:
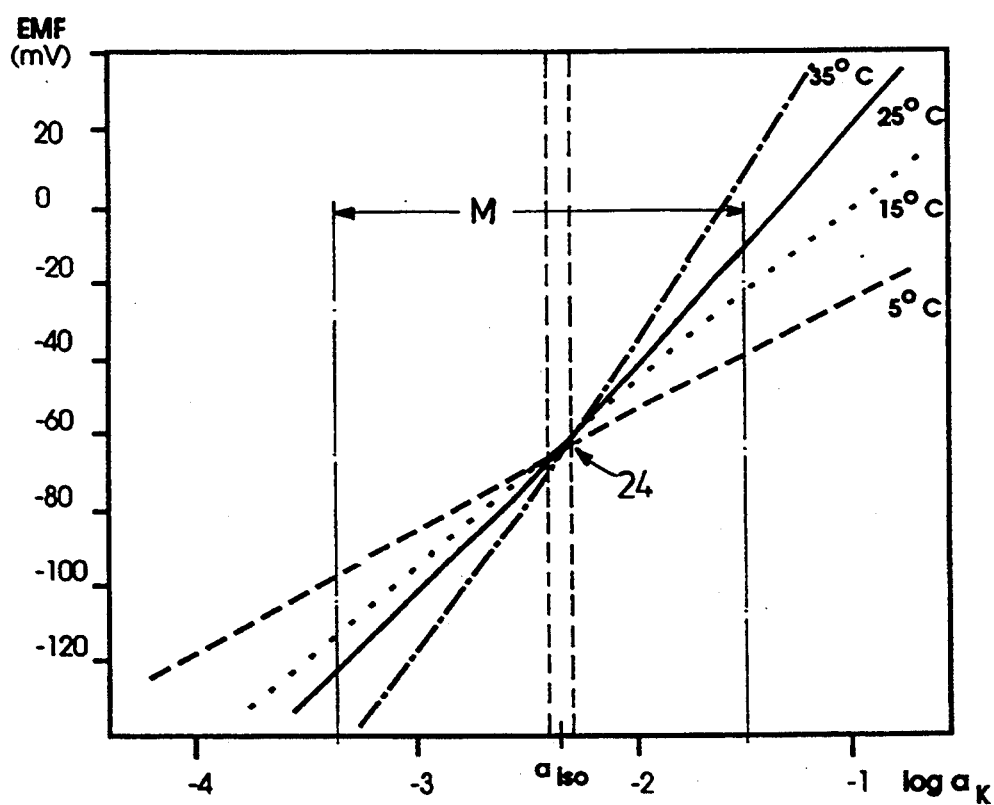
FIG. 4 is a graphical representation to illustrate the dependence of a measuring potential on the ion activity and the temperature.

The measuring electrodes 21 to 23, in their long-term stability, being subject to a certain drift expressing itself in some additive offset referred to the measured lines according FIG. 4, the measuring apparatus according to the invention can perform a subsequent calibration prior to the measuring electrodes 21 to 23 being used for measuring. Potential values are detected at any temperature by reference measurements of known reference solutions with the help of the respective measuring electrode 21 to 23, and with the aid of the stored calibrating regulation in the form of the qualitatively stored NERNST equation for instance, and of the data on the $E_0$ potential and on the scale factor C read-in from the bar code, they are converted into actual activity values and compared with the known set activity values of the corresponding ion in the reference solutions. If only some additive offset within certain narrow tolerances results, then the corresponding measuring electrode can be released for measuring and the measured values detected can be automatically corrected in accordance with the detected offset. If the offset is beyond pre-set limits, then the measurement can be stopped and a corresponding warning can be given for instance by the display.

What is claimed is:

1. An apparatus for a determination of at least one measured value of medical, electro-chemical and physical measured values relevant to organic or metabolic functions, comprising:
    a sensor head (1) with miniaturized measuring electrodes (21, 22, 23) for determining said at least one measured value, a temperature sensor (19) and at least one reference electrode (18),
    a coupling (2), to which the sensor head (1) is exchangeably secured and which has corresponding signal lines (15) to lead off electric measuring signals of the measuring electrodes (21, 22, 23) and of the temperature sensor (19),
    a microprocessor-controlled base instrument (5),
    a multicore cable (4) connecting said sensor head (1) via said coupling (2) to said base instrument (5),
    a central control unit (6) within said base/instrument (5) with a working memory, a program memory and a data memory for a control of operational processes within said apparatus,
    storage means within said base instrument (5) for storing at least one calibrating regulation which is associated to said at least one measured value,
    a data detection and evaluation unit (7) within the central control unit (6), to detect and convert said electric measuring signals forwarded by the coupling (2) into said at least one measured value by means of said at least one calibrating regulation,
    a display (8) connected to the central control until (6), for said at least one measured value determined by the data detection and evaluation unit (7), and
    a keyboard (11) connected to the base instrument (5), to enter measuring-relevant data,
    wherein each of said electro-chemical measuring electrodes (21, 22 23) has an activity-potential reference diagram with an isothermal point (24) and an activity measuring range (M) and
    wherein said sensor head (1) with said measuring electrodes (21, 22, 23) is precalibrated to standard by a manufacturer of said sensor head (1) such that in the activity-potential reference diagram the isothermal point (24) of each measuring electrode (21, 22, 23) lies within the activity measuring range (M) of each of said measuring electrodes (21, 22, 23).

2. An apparatus according to claim 1, comprising control means for controlling the access of the data detection and evaluation unit (7) to the at least one calibrating regulation by entering a code representative for each sensor head (1) and its measuring electrodes (21, 22, 23) via the keyboard (11) of the base instrument (5).

3. An apparatus according to claim 1, comprising a bar code reader (12), connected with the base instrument (5), and a bar code 13 applied on the sensor head (1), by which bar code reader (12) the bar code (13) is read as a code to control the access of the data detection and evaluation unit (7) to the at least one calibrating regulation.

4. An apparatus according to claim 1, comprising subsequent calibration means for a subsequent calibration of the precalibrated sensor head (1) prior to the latter's being used for measuring, actual values of activity measured at any temperature in reference solutions and determined by the at least one calibrating regulation being comparable with corresponding set values.

5. An apparatus according to claim 4, comprising an offset means for deriving an additive correction value from a variance comparison, which additive correction value is used for the evaluation of the measured values by the data detection and evaluation unit (7) during measuring.

6. An apparatus according to claim 1, wherein at least one electro-myelography electrode (20) is integrated in the sensor head (1).

* * * * *

UNITED STATES PATENT AND TRADEMARK OFFICE
CERTIFICATE OF CORRECTION

PATENT NO. : 5,425,361
DATED : June 20, 1995
INVENTOR(S) : Paul-Gerhard Fenzlein, et al It is certified that error appears in the above-indentified patent and that said Letters Patent is hereby corrected as shown below:

Column 7, line 42, after "base" delete "/"
Column 8, line 4, delete "until" and insert --unit--.

Signed and Sealed this

Ninth Day of January, 1996

Attest:

BRUCE LEHMAN

Attesting Officer          Commissioner of Patents and Trademarks